(12) United States Patent
Thompson

(10) Patent No.: US 9,849,010 B2
(45) Date of Patent: Dec. 26, 2017

(54) METHOD OF FORMING A NITINOL STENT

(71) Applicant: Medtronic Vascular, Inc., Santa Rosa, CA (US)

(72) Inventor: Dustin Thompson, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 15/135,947

(22) Filed: Apr. 22, 2016

(65) Prior Publication Data

US 2016/0235563 A1   Aug. 18, 2016

Related U.S. Application Data

(62) Division of application No. 13/403,784, filed on Feb. 23, 2012, now Pat. No. 9,345,596.

(51) Int. Cl.
| | |
|---|---|
| *B21F 45/00* | (2006.01) |
| *A61F 2/90* | (2013.01) |
| *A61F 2/88* | (2006.01) |
| *A61L 31/08* | (2006.01) |
| *A61L 31/16* | (2006.01) |
| *C21D 9/00* | (2006.01) |
| *C22F 1/00* | (2006.01) |
| *C22F 1/10* | (2006.01) |
| *C23F 1/12* | (2006.01) |

(Continued)

(52) U.S. Cl.
CPC .................. *A61F 2/90* (2013.01); *A61F 2/88* (2013.01); *A61L 31/022* (2013.01); *A61L 31/088* (2013.01); *A61L 31/16* (2013.01); *B21F 45/00* (2013.01); *B21F 45/008* (2013.01); *B23K 26/40* (2013.01); *C21D 9/0068* (2013.01); *C22F 1/006* (2013.01); *C22F 1/10* (2013.01); *C23F 1/12* (2013.01); *C23F 17/00* (2013.01); *A61F 2210/0014* (2013.01); *A61F 2240/001* (2013.01); *A61F 2250/0068* (2013.01); *A61F 2310/00023* (2013.01); *A61L 2300/406* (2013.01); *A61L 2300/41* (2013.01); *A61L 2300/416* (2013.01); *A61L 2300/42* (2013.01); *B23K 2203/14* (2013.01)

(58) Field of Classification Search
CPC ....... B21F 45/00; B21F 45/008; A61L 31/088
See application file for complete search history.

(56) References Cited

U.S. PATENT DOCUMENTS

| | | | |
|---|---|---|---|
| 4,800,882 A | 1/1989 | Gianturco |
| 4,886,062 A | 12/1989 | Wiktor |
| (Continued) |

*Primary Examiner* — R. K. Arundale
*Assistant Examiner* — Pradeep C Battula

(57) ABSTRACT

A method of a forming a hollow, drug-eluting nitinol stent includes shaping a composite wire into a stent pattern, wherein the composite wire includes an inner member, a nitinol intermediate member, and an outer member. After the composite wire is shaped into the stent pattern, the composite wire is heat treated to set the nitinol intermediate member in the stent pattern. After heat treatment, the composite wire is processed to remove the outer member and the inner member without adversely affecting the intermediate member. Openings may be provided through the intermediate member and the lumen of the intermediate member may be filled with a substance to be eluted through the openings.

20 Claims, 9 Drawing Sheets

(51) Int. Cl.
*C23F 17/00* (2006.01)
*A61L 31/02* (2006.01)
*B23K 26/40* (2014.01)
*B23K 103/14* (2006.01)

(56) References Cited

U.S. PATENT DOCUMENTS

| | | | |
|---|---|---|---|
| 5,019,090 A | 5/1991 | Pinchuk | |
| 5,133,732 A | 7/1992 | Wiktor | |
| 5,630,840 A | 5/1997 | Mayer | |
| 5,782,903 A | 7/1998 | Wiktor | |
| 6,136,023 A | 10/2000 | Boyle | |
| 6,248,190 B1 | 6/2001 | Stinson | |
| 6,279,368 B1* | 8/2001 | Escano | A61F 2/90 72/342.1 |
| 6,305,436 B1 | 10/2001 | Andersen | |
| 6,497,709 B1 | 12/2002 | Heath | |
| 6,527,802 B1* | 3/2003 | Mayer | A61F 2/86 623/1.1 |
| 7,008,446 B1* | 3/2006 | Amis | A61F 2/90 623/1.19 |
| 7,101,392 B2 | 9/2006 | Heath | |
| 7,984,636 B2* | 7/2011 | Obradovic | A61F 2/95 72/370.07 |
| 8,597,344 B2* | 12/2013 | Lundkvist | A61F 2/86 623/1.15 |
| 8,998,977 B2* | 4/2015 | Bienvenu | A61L 31/16 623/1.15 |
| 9,119,736 B2* | 9/2015 | Thompson | A61L 31/16 |
| 9,345,596 B2* | 5/2016 | Thompson | A61F 2/88 |
| 2004/0230288 A1* | 11/2004 | Rosenthal | A61F 2/07 623/1.13 |
| 2005/0059889 A1* | 3/2005 | Mayer | A61F 2/90 600/431 |
| 2005/0165468 A1 | 7/2005 | Marton | |
| 2006/0204556 A1* | 9/2006 | Daniels | A61L 31/06 424/443 |
| 2009/0151416 A1* | 6/2009 | Obradovic | A61F 2/95 72/264 |
| 2010/0269950 A1 | 10/2010 | Hoff et al. | |
| 2011/0008405 A1 | 1/2011 | Birdsall et al. | |
| 2011/0070357 A1 | 3/2011 | Mitchell et al. | |
| 2011/0070358 A1 | 3/2011 | Mauch et al. | |

* cited by examiner

METHOD OF FORMING A NITINOL STENT

RELATED APPLICATIONS

This application is a Division of and claims the benefit of U.S. patent application Ser. No. 13/403,784 filed Feb. 23, 2012, now allowed. The disclosures of which are herein incorporated by reference in their entirety.

FIELD OF THE INVENTION

The present invention relates to methods of making stents, and in particular, to methods of making stents from nitinol wires.

BACKGROUND OF THE INVENTION

Drug-eluting implantable medical devices have become popular in recent times for their ability to perform their primary function (such as structural support) and their ability to medically treat the area in which they are implanted. Further, stents made from shape memory materials, particularly nitinol, have become popular.

Stents formed from nitinol include many characteristics desirable in an effective stent. Nitinol is a nickel-titanium alloy generally containing approximately 55-56% nickel and 44-45% titanium. Nitinol was developed by the Naval Ordinance Laboratory and receives its name from its component parts and the Naval Ordinance Laboratory (Nickel/Titanium/Naval Ordinance Laboratory). Specifically, stents formed from nitinol, with or without special coatings, have been found to be chemically and biologically inert and to inhibit thrombus formation. Nitinol, under certain conditions, is also superelastic, which allows it to withstand extensive deformation and still resume its original shape. Furthermore, nitinol possesses shape memory, i.e., the metal "remembers" a specific shape fixed during a particular heat treatment and can resort to that shape under proper conditions.

The superelasticity of nitinol and its shape memory characteristics makes it possible to fabricate a stent having the desired shape and dimensions. Once formed, the stent can be temporarily deformed into a much narrower shape for insertion into the body. Once in place, the stent can be made to resume its desired shape and dimensions. Certain alloys of nickel and titanium can be made which are plastic at temperatures below about 30° C. and are elastic at body temperatures above 35° C. Such alloys are widely used for the production of stents for medical use since these nitinol stents are able to resume their desired shape at normal body temperature without the need to artificially heat the stent While using nitinol for stents is desirable, nitinol material presents some difficulties in the formation of the stent itself. Nitinol materials in either the cold worked or heat-treated state can be easily sheared or stamped, but they are difficult to form to an accurate geometry, whether by forming wire shapes or die pressing. Thus, many nitinol stents are formed from a nitinol tube that is laser cut to the shape of a stent, sometimes also known as a tubular slotted stent. However, many stents are formed by manipulating a wire into a desired stent shape. When forming such a stent from a nitinol wire, complicated or specific design fixtures are required to hold the nitinol wire in the desired pattern throughout the heat setting, or heat treatment, process cycle. Typical process steps when forming a nitinol wire to be used as a stent include: conforming the nitinol wire to the geometry of the fixture; placing the nitinol wire and fixture into a "furnace" or other heating device for a set temperature and duration; removing the nitinol wire and fixture from the heating device and quenching (flash cooling); and removing the nitinol wire from the fixture. Custom fixtures may be required for each particular stent design. It is also often difficult to generate a cost effective fixture for simple and complicated stent patterns. Simpler wire forming methods available for stents made from other materials, where controlled plastic deformation of the wire into the desired shape allows for the wire to hold its shape through further processing, are generally not available for use with nitinol wires. For example, and not by way of limitation, methods and devices for creating waveforms in a wire described in U.S. Application Publication Nos. 2010/0269950 to Hoff et al. and 2011/0070358 to Mauch et al., and co-pending U.S. application Ser. Nos. 13/191,134 and 13/190,775, filed Jul. 26, 2011, may not effectively be used to form nitinol wire stents.

Thus, there is a need for an improved method for forming a stent from a nitinol wire, and in particular, and improved method of forming a stent with a hollow nitinol wire.

SUMMARY OF INVENTION

Embodiments hereof relate to a method of forming a nitinol hollow wire stent. A composite wire including a core member, an intermediate nitinol member, and an outer member is shaped into a stent pattern. The outer member of the composite wire holds the intermediate nitinol member in the stent pattern until a heat treatment step is applied. The composite wire is heat treated to set the stent pattern into the intermediate nitinol member of the composite wire. The composite wire is then processed such that the outer member is removed from around the intermediate member without adversely affecting the intermediate member, such as by chemical etching. Openings may be provided through the intermediate member to a lumen of the intermediate member, or to the core member of the composite wire. The composite wire may also be processed to remove the core member from the lumen of the intermediate member without adversely affecting the intermediate member, and the lumen may be filled with a biologically or pharmacologically active substance.

Embodiments hereof also relate to a method of forming a stent with a solid nitinol wire. A composite wire including a solid nitinol inner member and an outer member is shaped into a stent pattern. The outer member of the composite wire holds the inner nitinol member in the stent pattern until the heat treatment step is completed. The composite wire is heat treated to set the nitinol inner member in the stent pattern. The composite wire is then processed such that the outer member is removed from around the inner member without adversely affecting the intermediate member, such as by chemical etching, thus leaving the solid nitinol inner member in the stent pattern.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Figure 1:
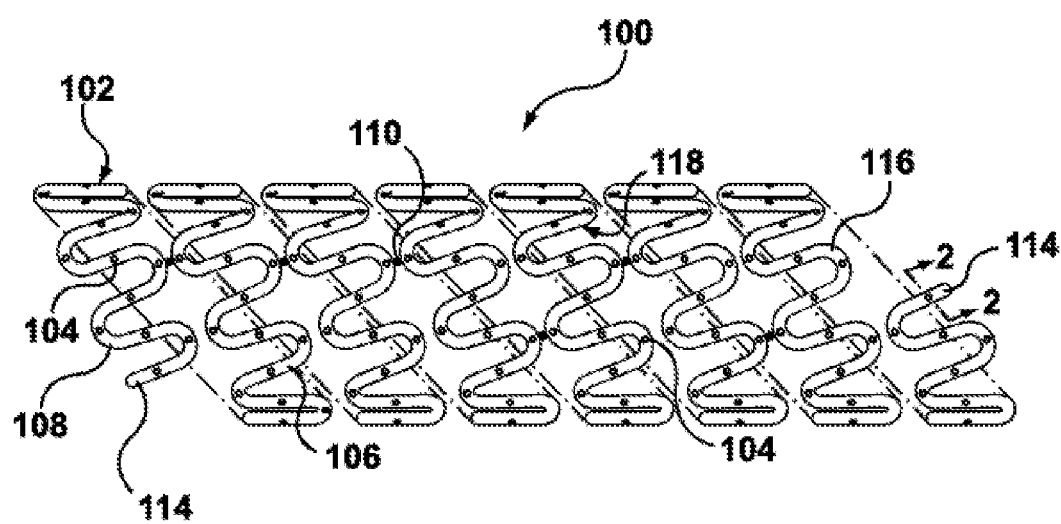
FIG. 1 is a schematic illustration of an exemplary stent in accordance with an embodiment hereof.
Figure 2:
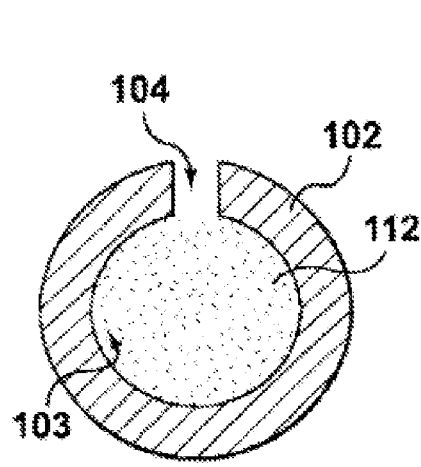
FIG. 2 is a cross-sectional view taken along line 2-2 of FIG. 1.
Figure 3:
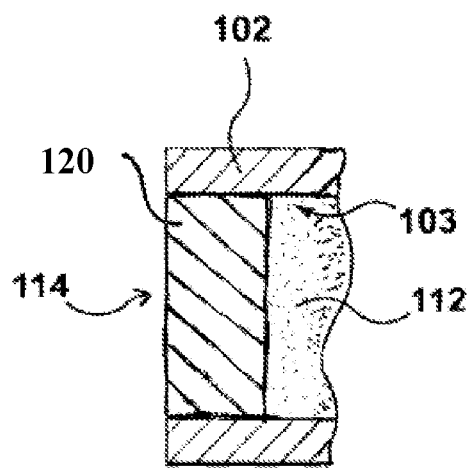
FIG. 3 is a longitudinal cross-section of an end of the wire of the stent of FIG. 1.
Figure 4:
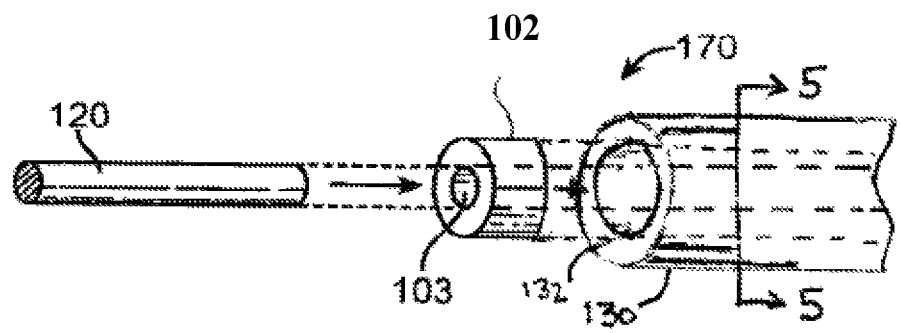
FIG. 4 is a schematic illustration of a composite wire including a core member, an intermediate member, and an outer member.

Specific embodiments of the present invention are now described with reference to the figures, where like reference numbers indicate identical or functionally similar elements. An embodiment of a stent 100 disclosed herein is shown in FIGS. 1-3. In particular, stent 100 is formed from a hollow wire 102, in particular, a hollow nitinol wire 102. The term "wire" as used herein means an elongated element or filament or group of elongated elements or filaments and is not limited to a particular cross-sectional shape or material, unless so specified. In the embodiment shown in FIG. 1, hollow wire 102 is formed into a series of generally sinusoidal waveforms including generally straight segments or struts 106 joined by bent segments or crowns 108. The wire with the waveforms formed therein is helically wrapped to form a tube, as shown in FIG. 1. In the embodiment shown in FIG. 1, selected crowns 108 of longitudinally adjacent sinusoids may be joined by, for example, fusion points 110. The invention hereof is not limited to the pattern shown in FIG. 1. Wire 102 of stent 100 can be formed into any pattern suitable for use as a stent. For example, and not by way of limitation, wire 102 of stent 100 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

As shown in FIG. 2, hollow wire 102 of stent 100 allows for a biologically or pharmacologically active substance 112 to be deposited within the lumen 103 of hollow wire 102. Although hollow wire 102 is shown as generally having a circular cross-section, hollow wire 102 may be generally elliptical or rectangular in cross-section. Hollow wire 102 further includes cuts or openings 104 dispersed along its length to permit biologically or pharmacologically active substance 112 to be released from lumen 103. Openings 104 may be disposed only on struts 106 of stent 100, only on crowns 108 of stent 100, or both struts 106 and crowns 108. Openings 104 may be sized and shaped as desired to control the elution rate of biologically or pharmacologically active substance 112 from stent 100. Larger sized openings 104 generally permit a faster elution rate and smaller sized openings 104 generally provide a slower elution rate. Further, the size and/or quantity of openings 104 may be varied along stent 100 in order to vary the quantity and/or rate of biologically or pharmacologically active substance 112 being eluted from stent 100 at different portions of stent 100. Openings 104 may be, for example and not by way of limitation, 5-30 µm in diameter. Openings 104 may be provided only on an outwardly facing or abluminal surface 116 of stent 100, as shown in FIG. 2, only on the inwardly facing or luminal surface 118 of stent 100, both surfaces, or may be provided anywhere along the circumference of wire 102. Openings 104 may have a constant diameter through the depth or have a tapered or conical shape.

Ends 114 of wire 102 may be closed, as shown in FIG. 3. Ends 114 may be closed by crimping excess material of wire 102 to close lumen 103. Closing ends 114 prevents drug 112 from prematurely releasing from ends 114. However, closing ends 114 is not required as drug 112 may be dried, provided within a polymer matrix, enclosed within a liner (not shown), or otherwise protected from premature release from ends 114. Further, ends 114 may be welded, crimped or otherwise connected to other portions of wire 102 such that the ends 114 are not free ends. Ends 114 may alternatively be provided as free ends. Further, ends 114 may be sealed by not removing the core member 120 from the ends of the wire, as shown in FIG. 3.

Figure 9:
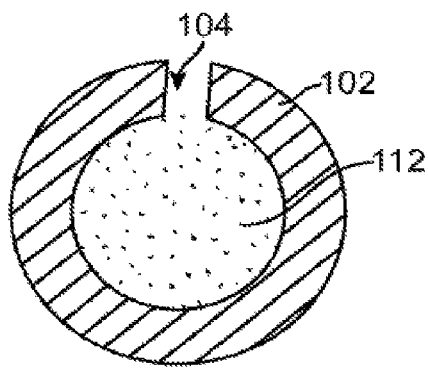
Figure 10:
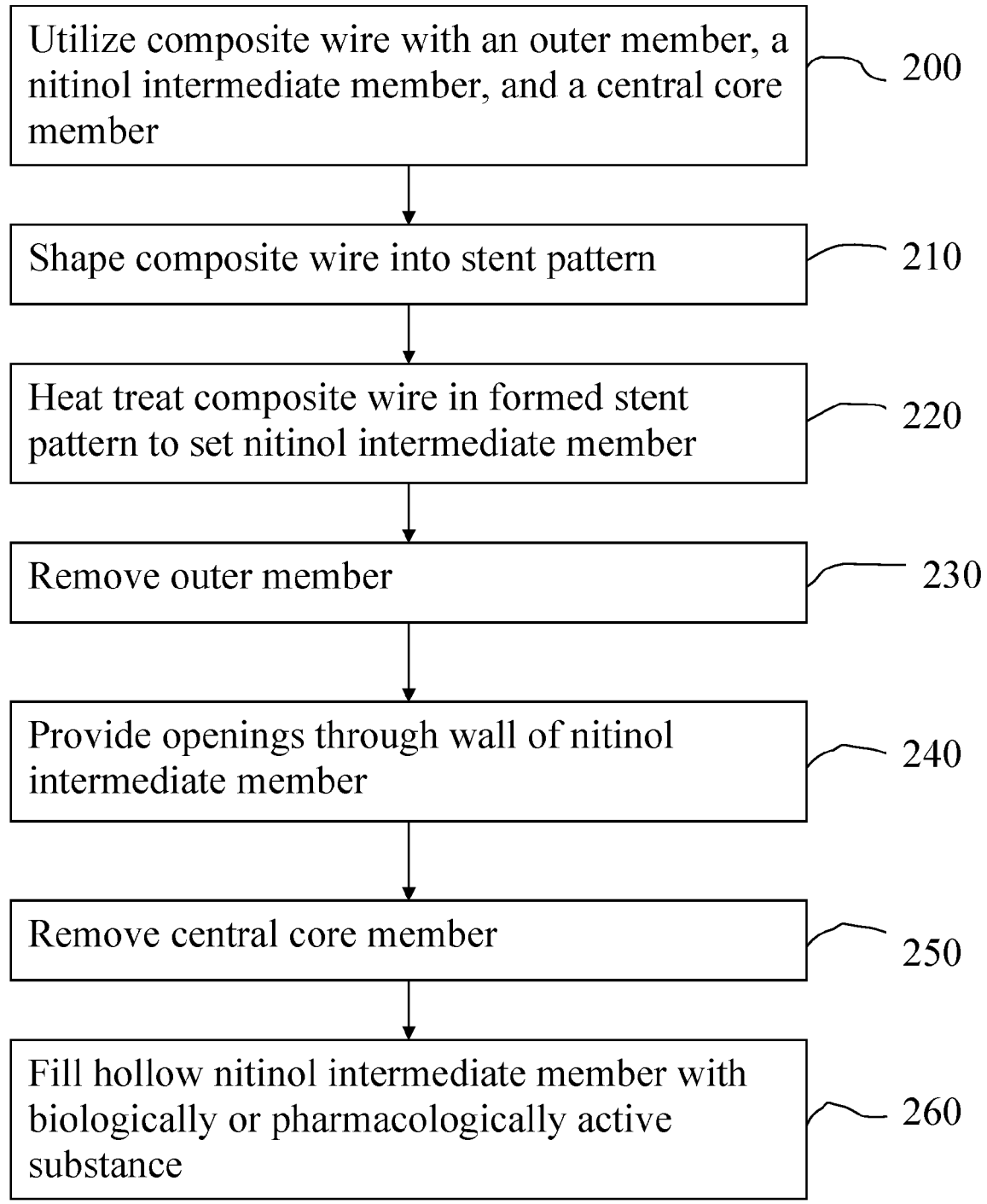
FIG. 10 is flow chart illustrating an embodiment of a method of forming a hollow Nitinol wire stent.

FIGS. 4-10 show a method for forming a hollow wire stent in accordance with an embodiment hereof. As shown in FIG. 10, step 200 is to utilize a wire having an outer member, an intermediate member, and a central core member. These types of wire are sometimes referred to as core wires, tri-layer wires, or composite wires. Composite wire 170 hereof is formed of an outer member 130, an intermediate member 102 disposed within a lumen 132 of outer member 130, and an inner or core member 120 disposed within a lumen 103 of intermediate member 102, as shown schematically in FIG. 4. Intermediate member 102 becomes hollow wire 102 of stent 100, and thus has been labeled with the same reference number. Composite wire 170 may be formed by any method known in the art, for example and not by way of limitation, a drawn filled tubing process, extrusion, cladding, material deposition, or any other suitable method. Examples of composite wires and methods of forming composite wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Intermediate member 102 in this embodiment is formed from nitinol. Intermediate member 102, as explained in more detail below, is the surviving material that will become hollow wire 102 of stent 100. Outer member 130 is formed from a material that is more plastically deformable than the nitinol material of intermediate member 102, and is sufficiently stiff to hold intermediate member 102 in the stent pattern until the heat treatment step, as described below. Further, the material used for outer member 130 must be able to be removed by a process that does not damage intermediate member 102. Similarly, core member 120 is made of a sacrificial material that can be removed by a process that does not damage the nitinol material of intermediate member 102. Core member 120 may be the same material as outer member 130, or may be a different material. In one non-limiting embodiment core member 120 and outer member 130 are made from tantalum. Examples of other materials for core member 120 and outer member 130 include, but are not limited to, tungsten (W), molybdenum (Mo), niobium (Nb), rhenium (Re), carbon (C), germanium (Ge), silicon (Si) and alloys thereof.

Figure 5:
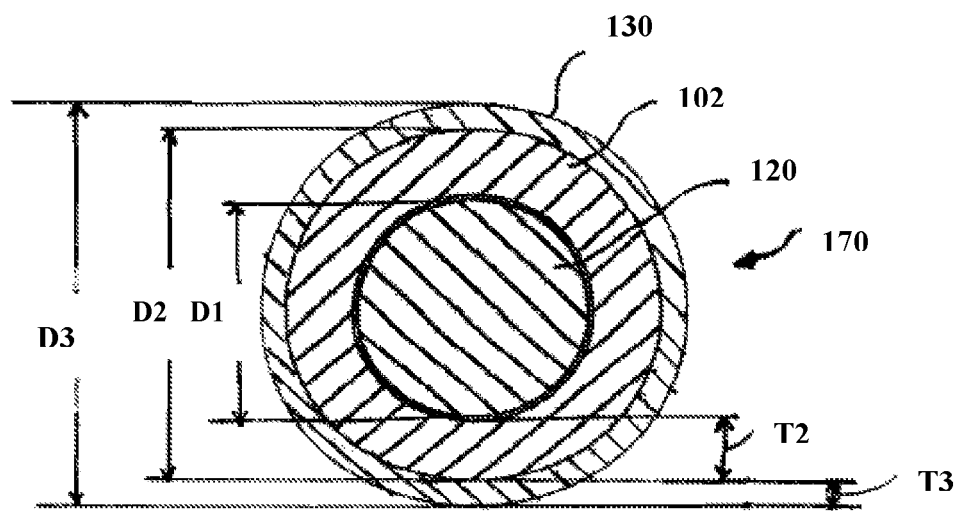
FIGS. 5-9 are cross-sectional views of the composite wire of FIG. 4 at various stages of an embodiment of a method of forming a hollow nitinol wire stent.

A cross-section of composite wire 170 is shown in FIG. 5. Intermediate member 102 may have an outer diameter D2 in the range of 0.0025 inch to 0.010 inch and wall thickness T2 in the range of 0.0005 inch or larger, depending on the application, for example, in what lumen or organ and for what purpose the stent is to be utilized. Accordingly, core member 120 may have an outer diameter D1 of 0.0005 inch to 0.0095 inch. Outer member 130 may have a thickness T3 in the range of 0.0001 inch or larger, depending on the material used for each member of composite wire 170. In one particular non-limiting example, core member 120 is made from tantalum and has an outer diameter D1 of 0.0020, intermediate member 102 is made from nitinol and has a thickness T2 of 0.0025 and an outer diameter D2 of 0.0070, and outer member 130 is made from tantalum and has a thickness T3 of 0.0005 and an outer diameter D3 of 0.0080. The values listed above are merely examples and other diameters and thicknesses may be used depending on, for example, the materials used, the desired stent shape, and the purpose or location of the stent.

Referring to FIG. 10, step 210 is to shape the composite wire 170 into the stent pattern. As discussed above, the stent pattern can be the pattern shown in FIG. 1 or any other suitable pattern formed from a wire. Further, although the order of all the steps is not critical, step 210 must be done prior to removing outer member 130, as explained in more detail below. However, the step of shaping the composite member 170 into the stent pattern does not have to include shaping composite member 170 into the final stent pattern. For example, the step 210 of shaping the composite member 170 into a stent pattern may include only forming the struts 106 and crowns 108 in composite wire 170, prior to the heat treating step described below. Shaping composite wire 170 into the stent pattern while outer member 130 is disposed around nitinol intermediate member 102 and core member 120 is disposed within intermediate member 102 allows for outer member 130 and core member 120 to "hold" nitinol intermediate member 102 in the stent pattern. As explained above, nitinol members generally must be held in the desired stent pattern using complicated, custom designed fixtures or jigs prior to the heat treating step. Utilizing outer member 130 and core member 120 eliminates the need for such complicated, custom designed fixtures or jigs. This holding function may be primarily accomplished by outer member 130. Thus, the step 210 of shaping composite wire 170 into the stent pattern can be performed with the same techniques used to shape conventional stents made from stainless steel, MP35N, or other known materials. For example, and not by way of limitation, shaping the composite wire 170 into the stent pattern shown in FIG. 1 generally includes the steps of forming composite wire 170 into a two dimensional sinusoid pattern followed by wrapping the pattern around a mandrel, as known to those skilled in the art. Forming the composite wire 170 into a two dimensional waveform can be achieved, for example, using techniques described in U.S. Application Publication Nos. 2010/0269950 to Hoff et al. and 2011/0070358 to Mauch et al., and co-pending U.S. application Ser. Nos. 13/191,134 and 13/190,775, filed Jul. 26, 2011, each of which is incorporated in its entirety by reference herein. Other techniques known to those skilled in the art could also be used.

Step 220 shown in FIG. 10 is to heat treat the composite wire 170 while in the shaped stent pattern. Heat treating the composite wire "sets" the nitinol intermediate member 102 in the stent pattern such that nitinol intermediate member 102 "remembers" the stent pattern. Accordingly, when stent 100 with intermediate member 102 as the hollow wire thereof is manipulated into a radially compressed configuration for insertion into a body lumen, such as by a sleeve, the stent 100 will return to the stent configuration of FIG. 1 upon release from the sleeve, thereby deploying into the radially expanded configuration at the treatment site, as known to those skilled in the art. The heat treatment step 220 may be performed, for example, in a furnace or similar heating equipment. The conditions for heat treatment step 220 are known to those skilled in the art. For example, and not by way of limitation, composite wire 170 may be placed in a furnace at 400° C.-500° C. for 15 minutes. Appropriate temperatures and durations for the heat treatment step are known to those skilled in the art.

When the heat treatment step 220 is completed, the composite wire 170 may be removed from the furnace and any fixture to which it was attached, for example, a mandrel. Step 230 is to process the composite wire such that outer member 130 is removed without adversely affecting the intermediate member, such as by chemical etching. Step 230 can be performed by any suitable process for removing outer member 130 while preserving intermediate member 102. In particular, subjecting composite wire 170 to xenon difluoride ($XeF_2$) gas at low pressure (1-6 Torr) and relatively high temperature (approximately 150° C.) causes the xenon difluoride ($XeF_2$) gas to react with a tantalum (Ta) outer member 103 to form $TaF_5$ and Xe gases. Xenon difluoride ($XeF_2$) gas reacts similarly with an outer member 130 made from tungsten, molybdenum, niobium, rhenium, carbon, germanium, and silicon. Other methods for removing outer member 130 may used, as described, for example, in U.S. Application Publication no. 2011/0008405 to Birdsall et al. and U.S. Application Publication No. 2011/0070358 to Mauch et al., wherein methods of removing core members are described, each published application incorporated by reference herein in its entirety. Such methods and materials, where appropriate, can be equally applied for removal of outer member 130. As examples, but not by way of limitation, methods such as wet chemical dissolution, solubilization, sublimation, and melting may be used with appropriate outer member/core member combinations.

Figure 6:
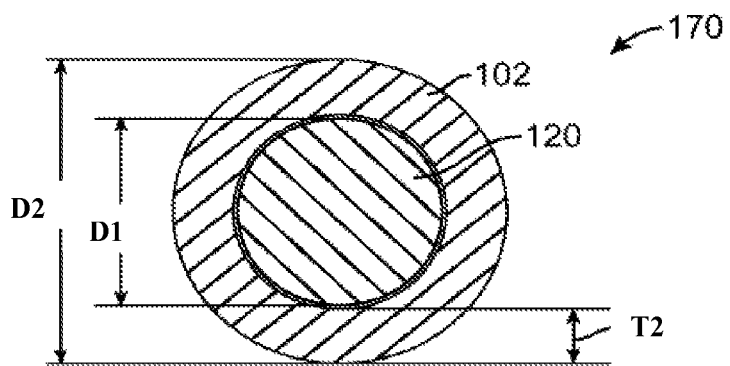

Upon completion of step 230 to etch outer member 130, intermediate member 102 and core member 120 remain in the shape of stent 100. A cross-section of composite member 170 includes intermediate member 102 and core member 120, as shown in FIG. 6. Further processing steps to finish, polish, and sterilize stent 100 may take place at this time, leaving a stent with a nitinol intermediate member 102 and a core member 120. In such a situation, core member 120 may be selected to improve a characteristic of nitinol intermediate member 102. For example, and not by way of limitation, core member 120 may be formed from a radiopaque material to improve radiopacity of the stent. For example, and not by way of limitation, core member 120 may be formed of tantalum or platinum, which are considered a radiopaque material, in order to improve the radiopacity of relatively radiolucent nitinol intermediate member 102.

Figure 7:
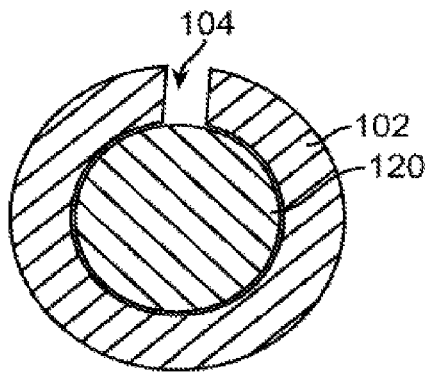
Figure 8:
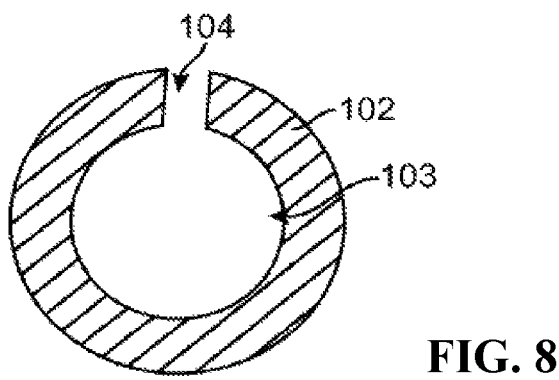

However, in order to provide a stent 100 with a hollow wire 102, as described above with respect to FIGS. 1-3, further processing is required. In particular, step 240 is to provide openings 104 in intermediate member 102 through to lumen 103 of intermediate member 102. Openings 104 may be laser cut, drilled, etched, or otherwise provided in intermediate member 102. Step 240 need not be performed after step 230, nor before step 250, although it is preferred to be before step 250, as explained in more detail below. If step 240 is performed after step 230, a cross-section of composite wire 170 will include intermediate member 102, core member 120, and an opening 104, as shown in FIG. 7. It should also be noted that step 240 of forming an opening 104 through intermediate member 102 can be performed prior to step 230 of chemically etching away outer member 130. In such a situation, the opening 104 may extend through outer member 130 and intermediate member 102 through to lumen 103 of intermediate member 102. Thus, the step 230 of chemically etching away outer member 130 will be combined with the step 250 of chemically etching away core member 120, described below. In such a situation, it is preferable that the material of outer member 130 and core member 120 may both be etched by the same etchant, such as, but not limited to, xenon difluoride.

Step 250 is to process composite wire 170 such that core member 120 is removed from the lumen 103 of intermediate member 102 without adversely affecting intermediate member 102, such as by chemical etching. Step 250 can be performed by any suitable process for removing core member 120 while preserving intermediate member 102. In particular, subjecting composite wire 170 to xenon difluoride ($XeF_2$) gas at low pressure (1-6 Torr) and relatively high temperature (approximately 150° C.) causes the xenon difluoride ($XeF_2$) gas to react with a tantalum (Ta) core member 120 to form $TaF_5$ and Xe gases, which can be exhausted from lumen 103. Xenon difluoride ($XeF_2$) gas reacts similarly with a core member 120 made from tungsten, molybdenum, niobium, rhenium, carbon, germanium, and silicon. However, xenon difluoride ($XeF_2$) gas does not react with an intermediate member formed of nitinol. Other methods for removing core member 120 may used, as described, for example, in U.S. Application Publication no. 2011/0008405 to Birdsall et al. and U.S. Application Publication No. 2011/0070358 to Mauch et al., each published application incorporated by reference herein in its entirety. As examples, but not by way of limitation, methods such as wet chemical dissolution, solubilization, sublimation, and melting may be used with appropriate intermediate member/core member combinations. Accordingly, after step 250 is completed, intermediate member 102 remains and core member 120 has been removed, leaving the structure shown in FIG. 8. As noted above, openings 104 do not need to be formed prior to the step of removing core member 120 as long as there is a way to expose core member 120 to the etchant. For example, ends 114 of the wire may be open or temporary ports may for formed through intermediate member 102 to expose core member 120 to the etchant.

After core member 120 has been removed, biologically or pharmacologically active substance 112 may be introduced into lumen 103 of intermediate member 102, as shown in step 260 of FIG. 10. This produces a hollow wire or intermediate member 102 with biologically or pharmacologically active substance 112 disposed in lumen 103 thereof, and openings 104 through which biologically or pharmacologically active substance 112 may be eluted, as shown in FIGS. 2 and 9. Filling lumen 102 with a biologically or pharmacologically active substance may be accomplished by any means known to those skilled in the art. For example, and not by way of limitation, methods for filling lumens of hollow wires described in U.S. Application Publication No. 2011/0070357 to Mitchell et al., each of which is incorporated by reference herein in its entirety; and co-pending U.S. application Ser. Nos. 12/884,362; 12/884,451; 12/884,501; 12/884,578; 12/884,596 each filed on Sep. 17, 2010, and each of which is incorporated by reference herein in its entirety.

The biologically or pharmacologically active substance 112 may include, but is not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suram in, serotonin blockers, steroids, thioprotease inhibitors, triazolopyrimidine (a PDGF antagonist), and nitric oxide. An example of an antiallergic agent is permirolast potassium. Other biologically or pharmacologically active substances or agents that may be used include nitric oxide, alpha-interferon, genetically engineered epithelial cells, and dexamethasone. In other examples, the biologically or pharmacologically active substance is a radioactive isotope for implantable device usage in radiotherapeutic procedures.

Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing biologically or pharmacologically active substances are well-known to those of ordinary skill in the art, the biologically or pharmacologically active substances are provided by way of example and are not meant to be limiting. Other biologically or pharmacologically active substances are equally applicable for use with the disclosed methods and compositions.

Further, a carrier may be used with the biologically or pharmacologically active substance. Examples of suitable carriers include, but are not limited to, urea, ethanol, acetone, tetrahydrofuran, dymethylsulfoxide, a combination thereof, or other suitable carriers known to those skilled in the art. Still further, a surfactant may be formulated with the biologically or pharmacologically active substance and the solvent to aid elution of the biologically or pharmacologically active substance.

Stent 100 may be used conventionally in blood vessels of the body to support such a vessel after an angioplasty procedure. It is known that certain biologically or pharmacologically active substances eluted from stents may prevent restenosis or other complications associated with angioplasty or stents. Stent 100 may alternatively be used in other organs or tissues of the body for delivery of biologically or pharmacologically active substance to treat tumors, inflammation, nervous conditions, or other conditions that would be apparent to those skilled in the art.

Figure 11:
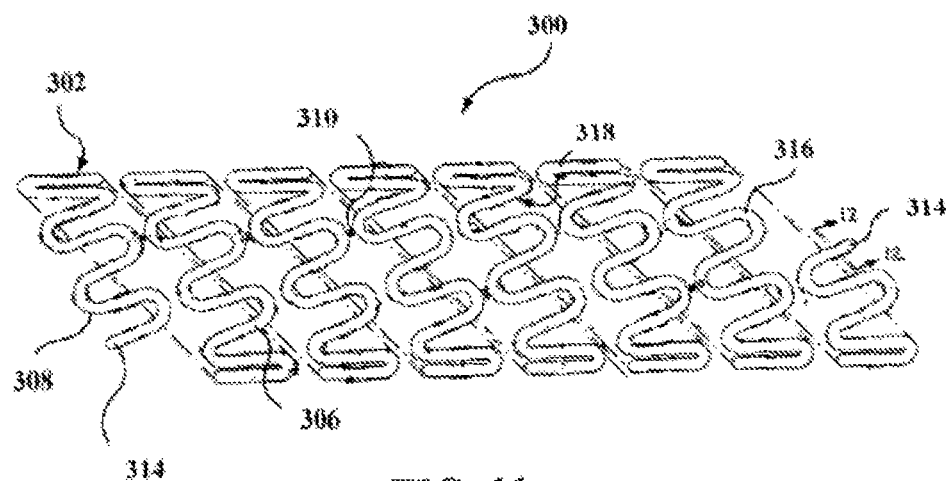
FIG. 11 is a schematic illustration of an exemplary stent in accordance with an embodiment hereof.
Figure 12:
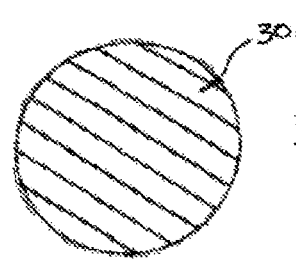
FIG. 12 is a cross-sectional view taken along line 12-12 of FIG. 11.
Figure 13:
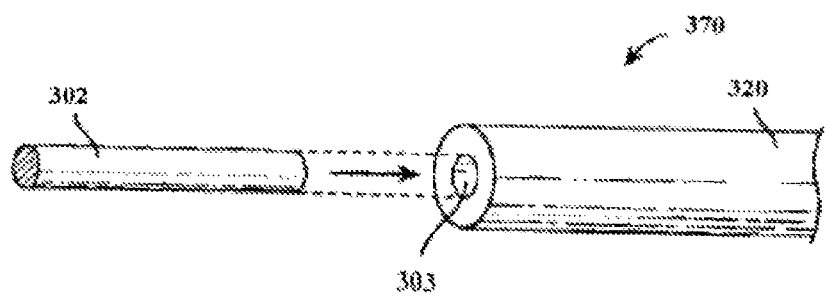
FIG. 13 is a schematic illustration of a composite wire including a nitinol core member and an outer member.

FIGS. 11-15 show an embodiment of a stent 300 formed using a solid nitinol wire 302. In particular, stent 300 is formed from a solid wire 302, as shown in FIG. 12. In the embodiment shown in FIG. 11, stent 300 is formed into a series of generally sinusoidal waves including generally straight segments or struts 306 joined by bent segments or crowns 308. The generally sinusoidal pattern is formed into a tube, as shown in FIG. 11. In the embodiment shown in FIG. 11, selected crowns 308 of longitudinally adjacent sinusoids may be joined by, for example, fusion points 310. The invention hereof is not limited to the pattern shown in FIG. 11. Wire 302 of stent 300 can be formed into any pattern suitable for use as a stent. For example, and not by way of limitation, wire 302 can be formed into patterns disclosed in U.S. Pat. No. 4,800,082 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety.

Ends 314 of wire 302 may be free ends, as shown in FIG. 11, or may be fused, crimped, or otherwise connected to other portions of wire 302, as known to those skilled in the art. Stent 300 may be coated with a biologically or pharmacologically active substance (not shown) or may be a bare stent. A coating may be disposed on a luminal surface 316, and abluminal surface 118, or both.

As explained above, forming stents from nitinol wire is often difficult due to complicated custom fixtures or jigs required to hold the nitinol wire in place during the heat treatment or heat setting process. In the method described herein with respect to FIGS. 11-15, the need for such complicated custom fixtures or jigs is alleviated. In particular, as shown in FIG. 15, step 400 is to utilize a wire with an outer member and a central core member. These types of wire are sometimes referred to as core wires or composite wires. Composite wire 370 hereof is formed of an outer member 320 and an inner or core member 302 disposed within a lumen 303 of outer member 320, as shown schematically in FIG. 13 and in cross-section in FIG. 14. Core member 302 becomes wire 302 of stent 300, and thus has been labeled with the same reference number. Composite wire 370 may be formed by any method known in the art, for example and not by way of limitation, a drawn filled tubing process, extruding the outer member over the inner member, or any other suitable method. Examples of core wires and methods of forming core wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Core member 302 is a nitinol material. Details regarding nitinol are provided above. Core member 302, as explained in more detail below, is the surviving material that will become wire 302. Outer member 320 may be a material that is more plastically deformable than nitinol and is sufficiently stiff to support core member 302 when composite wire 370 is deformed such that core member 302 does not revert back to its non-deformed shape. In particular, outer member 320 is formed from a material and of a selected thickness such that after composite wire 370 is bent into the stent pattern, as explained in more detail below, outer member 320 can "hold" core member 302 in the stent pattern without resort to complicated custom fixtures or jigs. Further, outer member 320 is made of a sacrificial material that can be removed by a process that does not damage the material of core member 302. Examples of materials for outer member 302 include, but are not limited to, tantalum (Ta), tungsten (W), molybdenum (Mo), niobium (Nb), rhenium (Re), carbon (C), germanium (Ge), silicon (Si) and alloys thereof.

Figure 14:
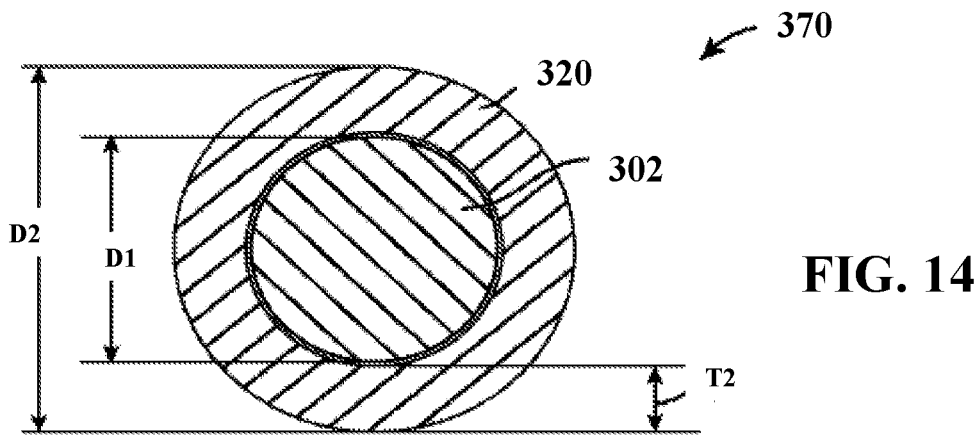
FIG. 14 is a cross-sectional view of the composite wire of FIG. 13.
Figure 15:
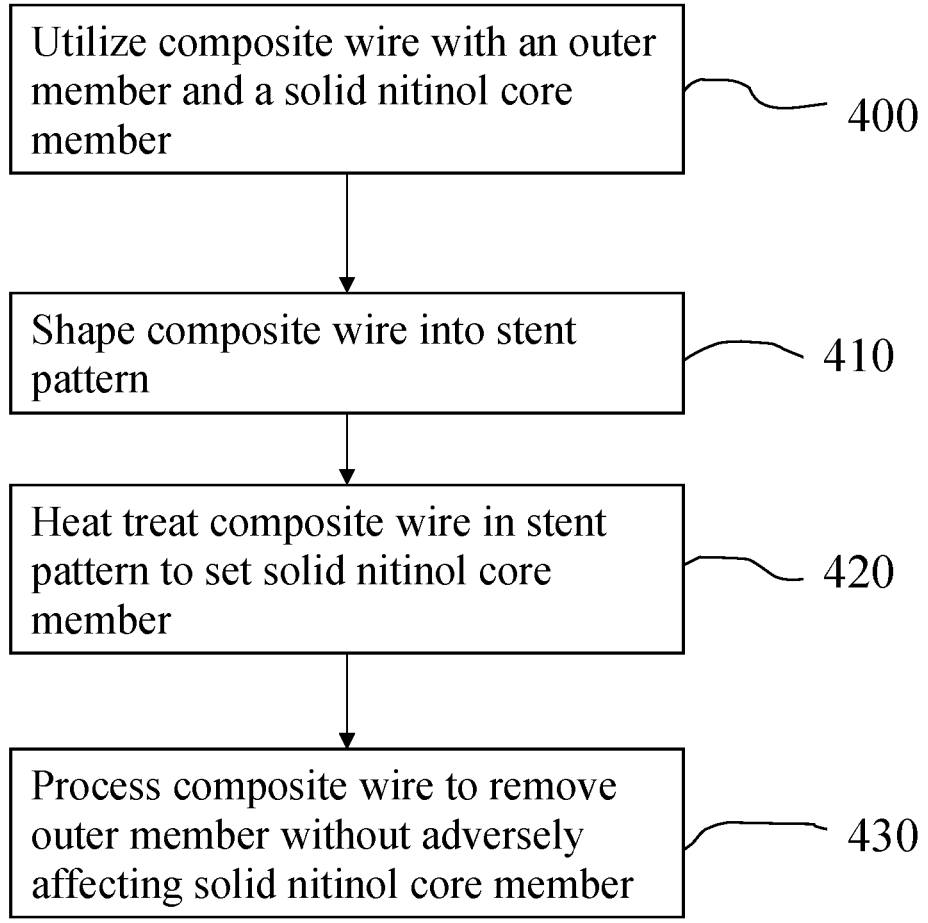
FIG. 15 is flow chart illustrating an embodiment of a method of forming a nitinol wire stent.

A cross-section of composite wire 370 is shown in FIG. 14. Core member 302 may have an outer diameter D1 in the range of 0.0025 inch to 0.0100 inch depending on the application, for example, in what lumen or organ and for what purpose the stent is to be utilized. Outer member 320 may have an outer diameter D2 in the range of 0.0030 inch to 0.0140 inch and wall thickness T2 in the range of 0.0002 to 0.0020 inch, depending on the size of core member 302 and the material selected for outer member 330. The values listed above are merely examples and other diameters and thicknesses may be used depending on, for example, the material used, the desired stent shape, and the purpose or location of the stent.

In one example, utilizing an outer member 320 formed from tantalum surrounding the Nitinol core member 302, the core member 302 may account for up to 90% of the overall outer diameter D2 and the tantalum outer member 320 would have sufficient stiffness to "hold" the Nitinol core member in place after shaping composite wire 370 into a stent pattern. In particular, the formula for stiffness is as follows:

$$\text{stiffness} \equiv \frac{F}{\delta} = \frac{F}{\left(\frac{FL^3}{3EI}\right)} = \frac{3EI}{L^3} = \frac{3E\left(\frac{1}{4}\pi r_2^4 - \frac{1}{4}\pi r_1^4\right)}{L^3}$$

where for solid circular cross section (core member 302) $I = \frac{1}{4}\pi r^4 = \frac{1}{64}\pi D1^4$ and for a tubular cross-section (outer member 320) $I = \frac{1}{4}\pi r_o^4 - \frac{1}{4}\pi r_i^4 = \frac{1}{64}\pi D2^4 - \frac{1}{64}\pi D1^4$. Thus, stiffness is proportional to EI. The chart below shows the inner diameter D1 of nitinol core member 302 as a percentage of the overall outer diameter D2 of the nitinol core member and the tantalum outer member 320. As can be seen, even with the nitinol core member 302 taking up 90% of the overall diameter D2, the outer member 302 (outer shell) is stiffer than core member 302.

| D1 as a % of D2 | 20% | 30% | 40% | 50% | 60% | 70% | 80% | 90% |
|---|---|---|---|---|---|---|---|---|
| Stiffness (EI) of Nitinol core member as a % of stiffness of tantalum outer member | 0.06% | 0.33% | 1.06% | 2.69% | 6.01% | 12.76% | 28.01% | 77.02% |

Referring back to FIG. 15, step 410 is to shape the composite wire 370 into the stent pattern. As discussed above, the stent pattern can be the pattern shown in FIG. 11 or any other suitable pattern formed from a wire. Further, although the order of all the steps is not critical, step 410 must be done prior to removing outer member 320, as explained in more detail below. Shaping composite wire 370 into the stent pattern while outer member 320 surrounds core member 302 permits outer member 320 to "hold" core member 302 in the stent pattern until the heat treatment step discussed below is completed. This alleviates the need for complicated custom fixtures or jigs to hold nitinol core member 302 in the stent pattern during the heat treatment step. Shaping the composite wire 370 into the stent pattern shown in FIG. 11 generally includes the steps of forming composite wire 370 into a two dimensional waveform or sinusoid pattern followed by wrapping the pattern around a mandrel, as known to those skilled in the art. Forming the composite wire 370 into a two dimensional waveform can be achieved, for example, using techniques described in U.S. Application Publication Nos. 2010/0269950 to Hoff et al. and 2011/0070358 to Mauch et al., and co-pending U.S. application Ser. Nos. 13/191,134 and 13/190,775, filed Jul. 26, 2011, each of which is incorporated in its entirety by reference herein. Other techniques known to those skilled in the art could also be used.

Step 420 shown in FIG. 15 is to heat treat the composite wire 370 while in the shaped stent pattern. Heat treating the composite wire "sets" the nitinol core member 302 in the stent pattern such that nitinol core member 302 "remembers" the stent pattern. Accordingly, when stent 300 with core member 302 as the wire thereof is manipulated into a radially compressed configuration for insertion into a body lumen, such as by a sleeve, the stent 300 will return to the stent configuration of FIG. 11 upon release from the sleeve, thereby deploying to the radially expanded configuration at the treatment site, as known to those skilled in the art. The heat treatment step 420 may be performed, for example, in a furnace or similar heating equipment. The conditions for heat treatment step 420 are known to those skilled in the art. For example, and not by way of limitation, composite wire 370 may be placed in a furnace at 400° C.-500° C. for 15 minutes. Appropriate temperatures and durations for the heat treatment step are known to those skilled in the art.

When the heat treatment step 420 is completed, the composite wire 370 may be removed from the furnace and any fixture to which it was attached, for example, a mandrel. Step 430 is to process composite wire 370 such that outer member 320 is removed from around core member 302 without adversely affecting core member 302, such as by chemical etching. Step 430 can be performed by any suitable process for removing outer member 320 while preserving core member 302. In particular, subjecting composite wire 370 formed of a nitinol core member 302 and a tantalum outer member 302 to xenon difluoride ($XeF_2$) gas at low pressure (1-6 Torr) and relatively high temperature (approximately 150° C.) causes the xenon difluoride ($XeF_2$) gas to react with the tantalum outer member 302 to form $TaF_5$ and Xe gases. Xenon difluoride ($XeF_2$) gas reacts similarly with an outer member 302 made from tungsten, molybdenum, niobium, rhenium, carbon, germanium, and silicon. Other methods for removing outer member 320 may used, as described, for example, in U.S. Application Publication no. 2011/0008405 to Birdsall et al. and U.S. Application Publication No. 2011/0070358 to Mauch et al., wherein methods of removing core members are described, each published application incorporated by reference herein in its entirety. Such methods and materials, where appropriate, can be equally applied for removal of outer member 320.

Removing outer member 320 leaves solid nitinol core member 302 formed in a stent pattern, as shown in FIGS. 11 and 12. Further processing of stent 300, such as polishing, sterilizing, and other steps known to those skilled in the art, may be performed to finish stent 300.

Figure 16:
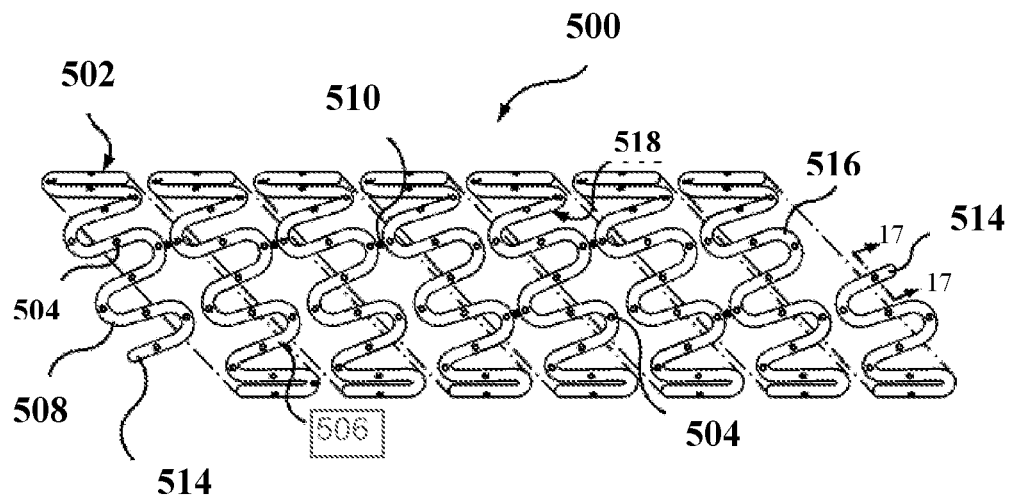
FIG. 16 is a schematic illustration of a stent in accordance with an embodiment hereof.
Figure 17:
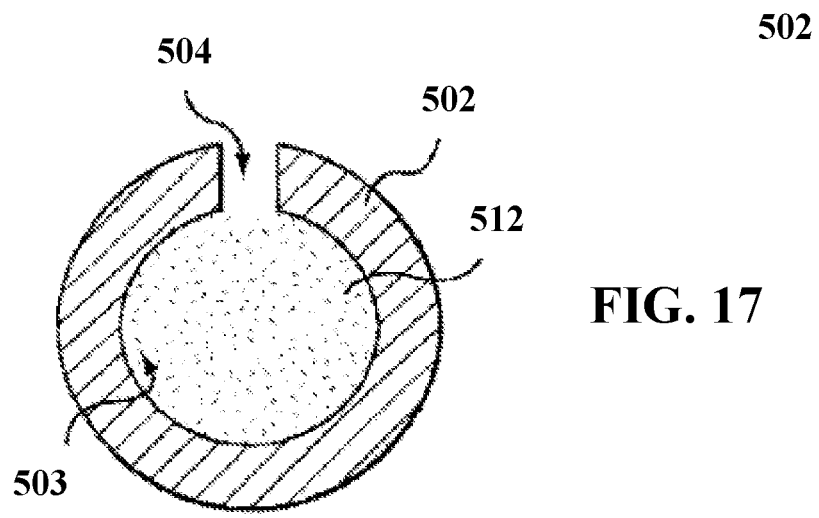
FIG. 17 is a cross-section view taken along line 17-17 of FIG. 16.
Figure 18:
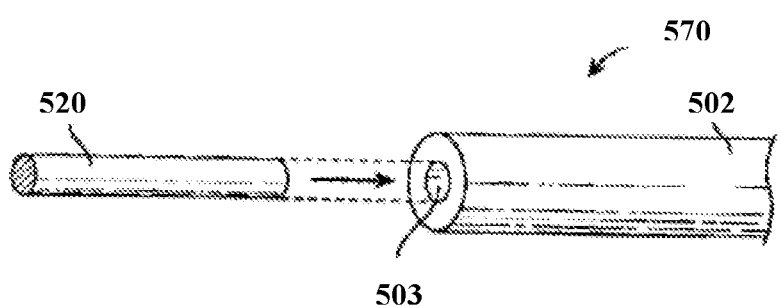
FIG. 18 is a schematic illustration of a composite within including a core member and a nitinol outer member.

An embodiment of a stent 500 disclosed herein is shown in FIGS. 16-17. In particular, stent 500 is formed from a hollow wire 502, in particular, a hollow nitinol wire 502. The term "wire" as used herein means an elongated element or filament or group of elongated elements or filaments and is not limited to a particular cross-sectional shape or material, unless so specified. In the embodiment shown in FIG. 16, hollow wire 502 is formed into a series of generally sinusoidal waveforms including generally straight segments or struts 506 joined by bent segments or crowns 508 and the wire with the waveforms formed therein is helically wound to form a generally tubular stent 500. In the embodiment shown in FIG. 16, selected crowns 508 of longitudinally adjacent sinusoids may be joined by, for example, fusion points 510. The invention hereof is not limited to the pattern shown in FIG. 16. Wire 502 of stent 500 can be formed into any pattern suitable for use as a stent. For example, and not by way of limitation, wire 502 of stent 500 can be formed into patterns disclosed in U.S. Pat. No. 4,800,882 to Gianturco, U.S. Pat. No. 4,886,062 to Wiktor, U.S. Pat. No. 5,133,732 to Wiktor, U.S. Pat. No. 5,782,903 to Wiktor, U.S. Pat. No. 6,136,023 to Boyle, and U.S. Pat. No. 5,019,090 to Pinchuk, each of which is incorporated by reference herein in its entirety. Further, instead of a single length of wire formed into a stent pattern, a plurality of wires may be formed into a two-dimensional waveform and wrapped into individual cylindrical elements. The cylindrical elements may then be aligned along a common longitudinal axis and joined to form the stent.

As shown in FIG. 17, hollow wire 502 of stent 500 allows for a biologically or pharmacologically active substance 512 to be deposited within the lumen 503 of hollow wire 502. Although hollow wire 502 is shown as generally having a circular cross-section, hollow wire 502 may be generally elliptical or rectangular in cross-section. Hollow wire 502 further includes cuts or openings 504 dispersed along its length to permit biologically or pharmacologically active substance 512 to be released from lumen 503. Openings 504 may be disposed only on struts 506 of stent 500, only on crowns 508 of stent 500, or both struts 506 and crowns 508. Openings 504 may be sized and shaped as desired to control the elution rate of biologically or pharmacologically active substance 512 from stent 500. Larger sized openings 504 generally permit a faster elution rate and smaller sized openings 504 generally provide a slower elution rate. Further, the size and/or quantity of openings 504 may be varied along stent 500 in order to vary the quantity and/or rate of biologically or pharmacologically active substance 512 being eluted from stent 500 at different portions of stent 500. Openings 504 may be, for example and not by way of limitation, 5-30 μm in diameter. Openings 504 may be provided only on an outwardly facing or abluminal surface 516 of stent 500, as shown in FIG. 17, only on the inwardly facing or luminal surface 518 of stent 500, both surfaces, or may be provided anywhere along the circumference of wire 502. Openings 504 may have a constant diameter through the depth or have a tapered or conical shape.

Ends 514 of wire 502 may be closed. Ends 114 may be closed by crimping excess material of wire 502 to close lumen 503. Closing ends 514 prevents drug 512 from prematurely releasing from ends 114. However, closing ends 114 is not required as drug 512 may be dried, provided within a polymer matrix, enclosed within a liner (not shown), or otherwise protected from premature release from ends 514. Further, ends 514 may be welded, crimped or otherwise connected to other portions of wire 502 such that the ends 514 are not free ends. Ends 514 may alternatively be provided as free ends. Further, ends 514 may be sealed by not removing the core member 520 from the ends of the wire.

Figure 19:
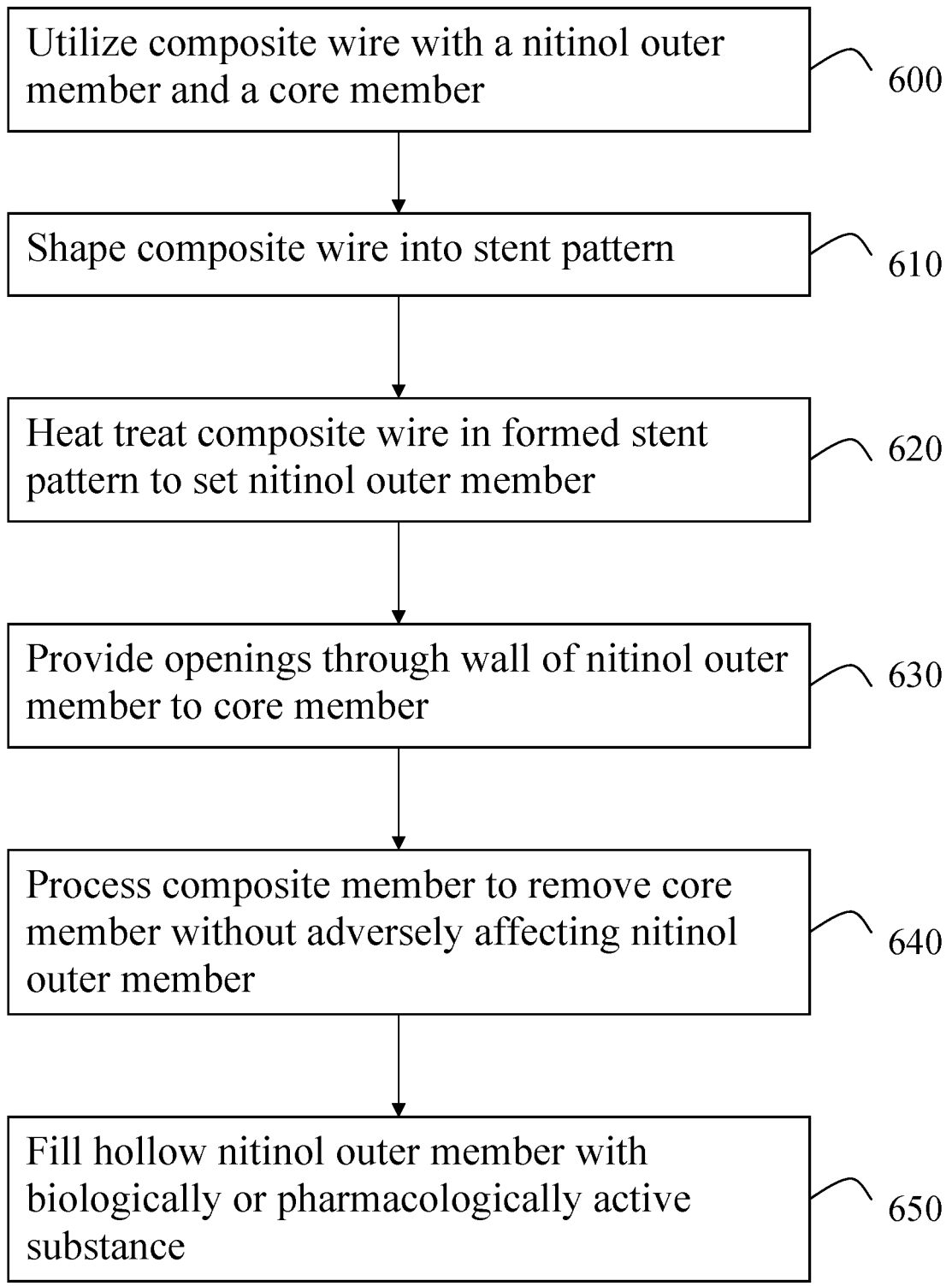
FIG. 19 is a flow chart illustrating steps in an embodiment of a method of forming a hollow nitinol wire stent.

FIGS. 18-23 show a method for forming a hollow nitinol wire stent 500 in accordance with an embodiment hereof. As shown in FIG. 19, step 600 is to utilize a wire having an outer member 102 and a central core member 120. These types of wire are sometimes referred to as core wires or composite wires. Composite wire 570 hereof is formed of an outer member 502 and a core member 520 disposed within a lumen 503 of outer member 502, as shown schematically in FIG. 18. Outer member 502 becomes hollow nitinol wire 502 of stent 500, and thus has been labeled with the same reference number. Composite wire 570 may be formed by any method known in the art, for example and not by way of limitation, a drawn filled tubing process, extrusion, cladding, material deposition, or any other suitable method. Examples of composite wires and methods of forming composite wires can be found in U.S. Pat. No. 5,630,840 to Mayer, U.S. Pat. No. 6,248,190 to Stinson, U.S. Pat. No. 6,497,709 to Heath, and U.S. Pat. No. 7,101,392 to Heath, each of which is incorporated by reference herein in its entirety.

Outer member 502 in this embodiment is formed from nitinol. Outer member 502, as explained in more detail below, is the surviving material that will become hollow nitinol wire 502 of stent 500. Core member 520 is formed from a material that is sufficiently stiff at the sizes provided to hold nitinol outer member 502 in the stent pattern until the heat treatment step, as described below. Core member 120 may also be formed of a material that is more plastically deformable than nitinol outer member 502. Further, the material used for core member 520 must be able to be removed by a process that does not damage nitinol outer member 502. In one non-limiting embodiment core member 520 is made from tungsten. Examples of other materials for core member 520 include, but are not limited to, tantalum, molybdenum, rhenium, and alloys thereof.

Figure 20:
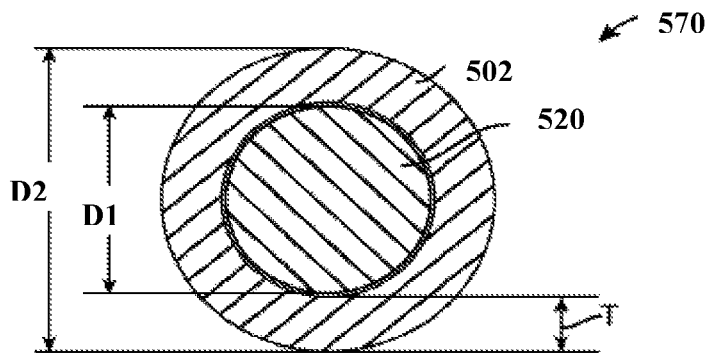
FIGS. 20-23 are cross-sectional views of a composite wire of FIG. 18 at various stages of the method of FIG. 19.

A cross-section of composite wire 570 is shown in FIG. 20. Outer member 502 may have an outer diameter D2 in the range of 0.0025 inch to 0.010 inch and wall thickness T in the range of 0.0005 inch or larger, depending on the application, for example, in what lumen or organ and for what purpose the stent is to be utilized. Accordingly, core member 520 may have an outer diameter D1 of 0.0005 inch to 0.0095 inch. In one particular non-limiting example, core member 520 is made from tungsten and has an outer diameter D1 of 0.0050 and outer member 502 is made from nitinol and has a thickness T of 0.0010 and an outer diameter D2 of 0.0070. The values listed above are merely examples and other diameters and thicknesses may be used depending on, for example, the materials used, the desired stent shape, and the purpose or location of the stent.

$$E_{core}I_{core} > E_{outer}I_{outer}$$

$$E_{core}D_1^4 > E_{outer}(D_2^4 - D_1^4)$$

where $E_{outer}$ would be the modulus of elasticity of Nitinol and $E_{core}$ would be the modulus of elasticity of the inner core material Referring to FIG. 19, step 610 is to shape the composite wire 570 into the stent pattern. As discussed above, the stent pattern can be the pattern shown in FIG. 16 or any other suitable pattern formed from a wire. Further, although the order of all the steps is not critical, step 610 must be done prior to removing core member 520, as explained in more detail below. However, the step of shaping the composite member 570 into the stent pattern does not have to include shaping composite member 570 into the final stent pattern. For example, the step 610 of shaping the composite member 570 into a stent pattern may include only forming the struts 506 and crowns 508 in composite wire 570, prior to the heat treating step described below. Shaping composite wire 570 into the stent pattern while core member 520 is disposed in the lumen of nitinol outer member 502 allows for core member 520 to "hold" nitinol outer member 502 in the stent pattern prior to an during the heat treating step described below. As explained above, nitinol members generally must be held in the desired stent pattern using complicated, custom designed fixtures or jigs prior to the heat treating step. Utilizing core member 520 eliminates the need for such complicated, custom designed fixtures or jigs. Thus, the step 610 of shaping composite wire 570 into the stent pattern can be performed with the same techniques used to shape conventional stents made from stainless steel, MP35N, or other known materials. For example, and not by way of limitation, shaping the composite wire 570 into the stent pattern shown in FIG. 16 generally includes the steps of forming composite wire 570 into a two dimensional sinusoid pattern followed by wrapping the pattern around a mandrel, as known to those skilled in the art. Forming the composite wire 570 into a two dimensional waveform can be achieved, for example, using techniques described in U.S. Application Publication Nos. 2010/0269950 to Hoff et al. and 2011/0070358 to Mauch et al., and co-pending U.S. application Ser. Nos. 13/191,134 and 13/190,775, filed Jul. 26, 2011, each of which is incorporated in its entirety by reference herein. Other techniques known to those skilled in the art could also be used.

Step 620 shown in FIG. 19 is to heat treat the composite wire 570 while in the shaped stent pattern. Heat treating the composite wire "sets" the nitinol outer member 502 in the stent pattern such that nitinol outer member 502 "remembers" the stent pattern. Accordingly, when stent 500 with nitinol outer member 502 as the hollow wire thereof is manipulated into a radially compressed configuration for insertion into a body lumen, such as by a sleeve, the stent 500 will return to the stent configuration of FIG. 16 upon release from the sleeve, thereby deploying into the radially expanded configuration at the treatment site, as known to those skilled in the art. The heat treatment step 620 may be performed, for example, in a furnace or similar heating equipment. The conditions for heat treatment step 620 are known to those skilled in the art. For example, and not by way of limitation, composite wire 570 may be placed in a furnace at 400° C.-500° C. for 15 minutes. Appropriate temperatures and durations for the heat treatment step are known to those skilled in the art.

Figure 21:
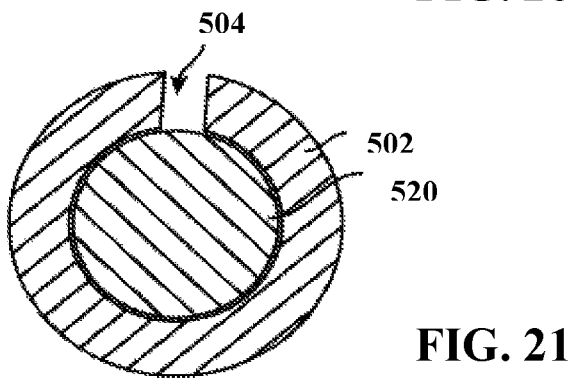
Figure 22:
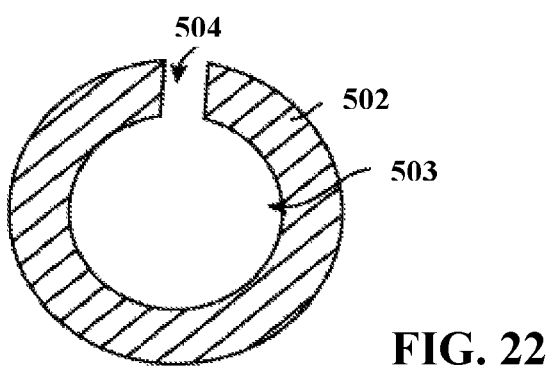

When the heat treatment step 620 is completed, the composite wire 570 may be removed from the furnace and any fixture to which it was attached, for example, a mandrel. Step 630 is to provide openings 504 in nitinol outer member 502 through to lumen 503 of nitinol outer member 502. Openings 504 may be laser cut, drilled, etched, or otherwise provided in outer member 502. Step 630 need not be performed after step 620, nor before step 640, although it is preferred to be before step 640, as explained in more detail below. If step 630 is performed after step 620, a cross-section of composite wire 570 will include outer member 502, core member 520, and an opening 504, as shown in FIG. 21. It should also be noted that step 630 of forming openings 504 through outer member 502 can be performed prior to step 610 of shaping the composite wire 570 into the stent pattern.

Step 640 is to process composite wire 570 such that core member 520 is removed from the lumen 503 of outer member 502 without adversely affecting outer member 502, such as by chemical etching. Step 640 can be performed by any suitable process for removing core member 520 while preserving outer member 502. In particular, subjecting composite wire 570 to xenon difluoride ($XeF_2$) gas at low pressure (1-6 Torr) and relatively high temperature (approximately 150° C.) causes the xenon difluoride ($XeF_2$) gas to react with a tungsten core member 520 to form $TaF_5$ and Xe gases, which can be exhausted from lumen 103. Xenon difluoride ($XeF_2$) gas reacts similarly with a core member 120 made from tantalum, molybdenum, rhenium, and alloys thereof. However, xenon difluoride ($XeF_2$) gas does not react with an intermediate member formed of nitinol. Other methods for removing core member 520 may used, as described, for example, in U.S. Application Publication no. 2011/0008405 to Birdsall et al. and U.S. Application Publication No. 2011/0070358 to Mauch et al., each published application incorporated by reference herein in its entirety. As examples, but not by way of limitation, methods such as wet chemical dissolution, solubilization, sublimation, and melting may be used with appropriate outer member/core member combinations. Accordingly, after step 640 is completed, outer member 502 remains and core member 520 has been removed, leaving the structure shown in FIG. 22. As noted above, openings 504 do not need to be formed prior to the step of removing core member 520 as long as there is a way to expose core member 520 to the etchant. For example, ends 514 of the wire may be open or temporary ports may be formed through outer member 502 to expose core member 520 to the etchant.

Figure 23:
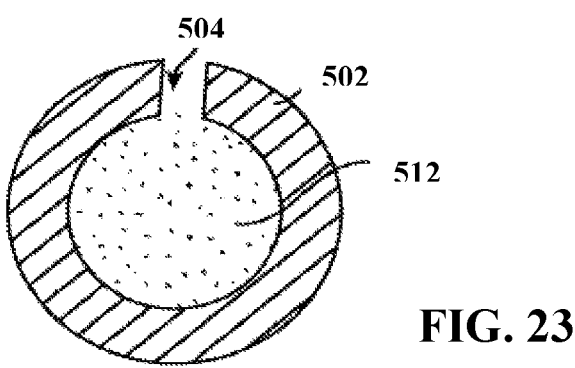

After core member 520 has been removed, biologically or pharmacologically active substance 512 may be introduced into lumen 503 of outer member 502, as shown in step 650 of FIG. 19. This produces a hollow wire or outer member 502 with biologically or pharmacologically active substance 512 disposed in lumen 503 thereof, and openings 504 through which biologically or pharmacologically active substance 512 may be eluted, as shown in FIGS. 17 and 23. Filling lumen 503 with a biologically or pharmacologically active substance may be accomplished by any means known to those skilled in the art. For example, and not by way of limitation, methods for filling lumens of hollow wires described in U.S. Application Publication No. 2011/0070357 to Mitchell et al., which is incorporated by reference herein in its entirety; and co-pending U.S. application Ser. Nos. 12/884,362; 12/884,451; 12/884,501; 12/884,578; 12/884,596 each filed on Sep. 17, 2010, and each of which is incorporated by reference herein in its entirety.

The biologically or pharmacologically active substance 512 may include, but is not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S. A., Frankfurt, Germany), methotrexate, azathioprine, vincristine, vinblastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include ABT-578 (a synthetic analog of rapamycin), rapamycin (sirolimus), zotarolimus, everolimus, angiopeptin, angiotensin converting enzyme inhibitors such as captopril (e.g., Capoten® and Capozide® from Bristol-Myers Squibb Co., Stamford, Conn.), cilazapril or lisinopril (e.g., Prinivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other biologically or pharmacologically active substances or agents that may be used include nitric oxide, alpha-interferon, genetically engineered epithelial cells, and dexamethasone. In other examples, the biologically or pharmacologically active substance is a radioactive isotope for implantable device usage in radiotherapeutic procedures. Examples of radioactive isotopes include, but are not limited to, phosphorus ($P^{32}$), palladium ($Pd^{103}$), cesium ($Cs^{131}$), Iridium ($I^{192}$) and iodine ($I^{125}$). While the preventative and treatment properties of the foregoing biologically or pharmacologically active substances are well-known to those of ordinary skill in the art, the biologically or pharmacologically active substances are provided by way of example and are not meant to be limiting. Other biologically or pharmacologically active substances are equally applicable for use with the disclosed methods and compositions.

Further, a carrier may be used with the biologically or pharmacologically active substance. Examples of suitable carriers include, but are not limited to, urea, ethanol, acetone, tetrahydrofuran, dymethylsulfoxide, a combination thereof, or other suitable carriers known to those skilled in the art. Still further, a surfactant may be formulated with the biologically or pharmacologically active substance and the solvent to aid elution of the biologically or pharmacologically active substance.

Stent 500 may be used conventionally in blood vessels of the body to support such a vessel after an angioplasty procedure. It is known that certain biologically or pharmacologically active substances eluted from stents may prevent restenosis or other complications associated with angioplasty or stents. Stent 500 may alternatively be used in other organs or tissues of the body for delivery of biologically or pharmacologically active substance to treat tumors, inflammation, nervous conditions, or other conditions that would be apparent to those skilled in the art.

While various embodiments of the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. Furthermore, there is no intention to be bound by any expressed or implied theory presented in the preceding technical field, background, brief summary or the detailed description. All patents and publications discussed herein are incorporated by reference herein in their entirety.

What is claimed is:

1. A method of forming a stent comprising the steps of:
shaping a composite wire into a stent pattern having a defined stent lumen, wherein the composite wire comprises a co-extruded core member and an outer member, wherein the outer member is a nitinol material and the core member is a material having a stiffness that holds the nitinol member in the stent pattern prior to a heat treatment step;
setting the nitinol outer member into the stent pattern by heat treating the composite wire while the core member holds the nitinol outer member in the stent pattern, wherein the core member material alone, due to its stiffness, holds the outer member in the stent pattern;
providing openings through the outer member to a lumen of the outer member;
processing the composite wire such that the core member is removed from the outer member while preserving the outer member in the stent pattern.

2. The method of claim 1, wherein the step of providing openings through the outer member comprises laser drilling openings through the outer member.

3. The method of claim 1, wherein the core member comprises a material selected from the group consisting of tungsten and molybdenum, and wherein the step of processing the composite wire to remove the inner member comprises exposing the composite wire to xenon difluoride gas.

4. The method of claim 1, further comprising the step of filling the lumen of the outer member with a biologically or pharmacologically active substance after the core member has been removed.

5. The method of claim 4, wherein the substance is selected from the group consisting of antineoplastic, antimitotic, antiinflammatory, antiplatelet, anticoagulant, anti fibrin, antithrombin, antiproliferative, antibiotic, antioxidant, and antiallergic substances as well as combinations thereof.

6. The method of claim 1, wherein a diameter of the core member is in the range of 0.0005 inch to 0.0095 inch.

7. The method of claim 1, wherein an outer diameter of the outer member is in the range of 0.0025 inch to 0.010 inch.

8. The method of claim 7, wherein the outer member has a thickness of at least 0.0005 inch.

9. The method of claim 1, wherein the core member is more plastically deformable than the outer member.

10. The method of claim 1, wherein the core member is tungsten.

11. The method of claim 10, wherein the core member has an outer diameter of about 0.0050 inch.

12. The method of claim 11, wherein the outer member has a wall thickness of about 0.0010 inch such that the outer member has an outer diameter of about 0.0070 inch.

13. A method of forming a stent comprising the steps of:
shaping a composite wire into a stent pattern having a defined stent lumen, wherein the composite wire comprises a co-extruded core member and an outer member, wherein the outer member is a nitinol material and the core member is a material having a stiffness that holds the nitinol member in the stent pattern prior to a heat treatment step;
setting the nitinol outer member into the stent pattern by heat treating the composite wire while the core member holds the nitinol outer member in the stent pattern, wherein the setting by heat treating step is performed solely with the use of the core member to hold the composite wire in the stent pattern;
providing openings through the outer member to a lumen of the outer member;
processing the composite wire such that the core member is removed from the outer member while preserving the outer member in the stent pattern.

14. The method of claim 13, wherein the core member comprises a material selected from the group consisting of tungsten and molybdenum, and wherein the step of processing the composite wire to remove the inner member comprises exposing the composite wire to xenon difluoride gas.

15. The method of claim 13, wherein a diameter of the core member is in the range of 0.0005 inch to 0.0095 inch.

16. The method of claim 13, wherein an outer diameter of the outer member is in the range of 0.0025 inch to 0.010 inch.

17. The method of claim 16, wherein the outer member has a thickness of at least 0.0005 inch.

18. The method of claim 13, wherein the core member is more plastically deformable than the outer member.

19. The method of claim 13, wherein the core member is tungsten.

20. The method of claim 19, wherein the core member has an outer diameter of about 0.0050 inch.

* * * * *